(12) United States Patent
Andree et al.

(10) Patent No.: US 6,417,141 B1
(45) Date of Patent: Jul. 9, 2002

(54) SUBSTITUTED AMINOURACILS

(75) Inventors: Roland Andree; Mark Wilhelm Drewes, both of Langenfeld; Otto Schallner, Monheim; Markus Dollinger; Hans-Joachim Santel, both of Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/000,038

(22) PCT Filed: Jul. 15, 1996

(86) PCT No.: PCT/EP96/03088

§ 371 (c)(1),
(2), (4) Date: Jan. 21, 1998

(87) PCT Pub. No.: WO97/05116

PCT Pub. Date: Feb. 13, 1997

(30) Foreign Application Priority Data

Jul. 28, 1995 (DE) .......................................... 195 27 570

(51) Int. Cl.⁷ ...................... A01N 43/54; C07D 239/54; C07D 239/96; C07D 405/12; C07D 239/95
(52) U.S. Cl. .................. 504/243; 544/309; 544/310; 544/311; 544/312; 544/313; 544/314; 544/317; 544/321; 544/323; 544/229; 544/295; 544/296; 544/238
(58) Field of Search .................. 544/309, 310–314, 544/317, 321, 323; 504/243

(56) References Cited

U.S. PATENT DOCUMENTS 6,077,813 A  6/2000 Linker et al. ............... 504/272

FOREIGN PATENT DOCUMENTS

| CA | 2210909 | 7/1997 |
| DE | 195 00 439 | 11/1995 |
| EP | 0 517 181 | 12/1992 |
| WO | WO 95/30661 | 11/1995 |
| WO | WO 96/24590 | 8/1996 |

*Primary Examiner*—Jose' G. Dees
*Assistant Examiner*—Sabiha N. Qazi
(74) *Attorney, Agent, or Firm*—Norris McLaughlin & Marcus

(57) ABSTRACT

The invention relates to novel aminouracils of the general formula (I)

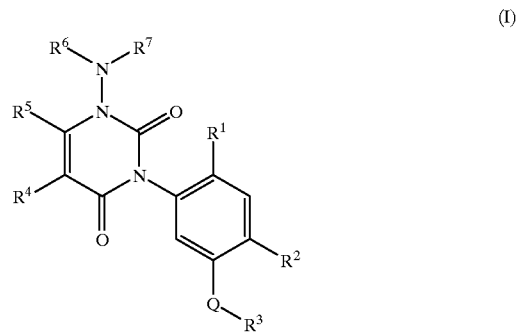

in which,

Q, $R^1$, $R^2$, $R^3$, $R^4$, $R^5$, $R^6$ and $R^7$ are each as defined in the description, to their use as herbicides and to novel intermediates.

6 Claims, No Drawings

SUBSTITUTED AMINOURACILS

The invention relates to novel substituted aminouracils, to processes for their preparation, to their use as herbicides and to novel intermediates.

It is known that certain substituted uracils have herbicidal properties (cf. EP 408382/U.S. Pat. No. 5,084,084/U.S. Pat. No. 5,127,935/U.S. Pat. No. 5,154,755, EP 563384, EP 648749, WO 91/00278, U.S. Pat. No. 497998 [illegible], U.S. Pat. No. 5,169,430). However, these compounds have hitherto not attained any major importance.

This invention, accordingly, provides the novel substituted aminouracils of the general formula (I)

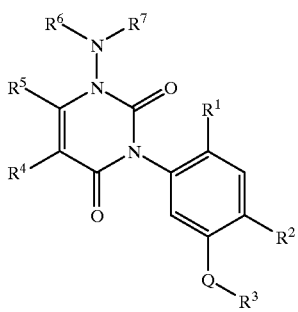

(I)

in which

Q represents O, S, SO or $SO_2$, $R^1$ represents hydrogen, cyano or halogen, $R^2$ represents cyano or thiocarbamoyl, $R^3$ represents hydrogen or represents respectively optionally substituted alkyl, alkenyl, alkinyl, cycloalkyl, cycloalkylalkyl, aryl, arylalkyl, heterocyclyl or heterocyclylalkyl, $R^4$ represents hydrogen, halogen or represents respectively optionally substituted alkyl or alkoxy, $R^5$ represents optionally substituted alkyl, $R^6$ represents hydrogen or represents respectively optionally substituted alkyl, alkenyl or alkinyl, and $R^7$ represents hydrogen or represents respectively optionally substituted alkyl, alkenyl or alkinyl.

The novel substituted aminouracils of the general formula (I) are obtained when (a) substituted uracils of the general formula (II)

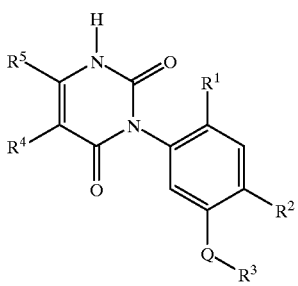

(II)

in which

Q, $R^1$, $R^2$, $R^3$, $R^4$ and $R^5$ are each as defined above are reacted with an electrophilic aminating agent, if appropriate in the presence of a reaction auxiliary, and if appropriate in the presence of a diluent, or (b) aminouracils of the general formula (Ia)

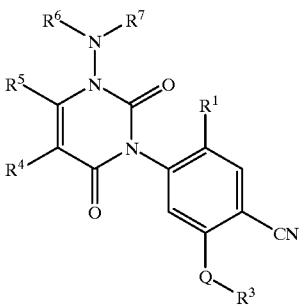

(Ia)

in which

Q, $R^1$, $R^3$, $R^4$, $R^5$, $R^6$ and $R^7$ are each as defined above are reacted with hydrogen sulphide, if appropriate in the presence of a reaction auxiliary and if appropriate in the presence of a diluent, or (c) aminouracils of the general formula (1b)

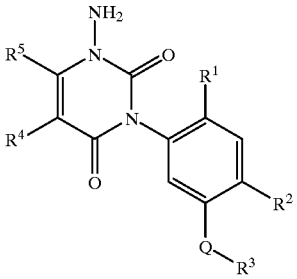

(Ib)

in which

Q, $R^1$, $R^2$, $R^3$, $R^4$ and $R^5$ are each as defined above are reacted with an alkylating agent of the formula (IIIa) and/or of the formula (IIIb)

$$X-R^7 \quad \text{(IIIa)}$$

$$X-R^8 \quad \text{(IIIb)}$$

in which $R^7$ and $R^8$ are each as defined above and

X represents halogen or the grouping $-O-SO_2-O-R^7$ or $-O-SO_2-O-R^8$, if appropriate in the presence of a reaction auxiliary and if appropriate in the presence of a diluent, or (d) aminouracils of the general formula (IV)

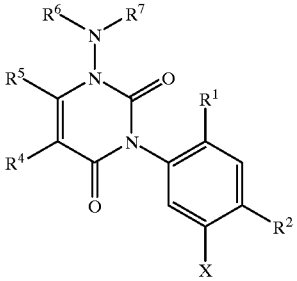

(IV)

in which $R^1$, $R^2$, $R^4$, $R^5$, $R^6$ and $R^7$ are each as defined above and X represents halogen, are reacted with nucleophilic compounds of the general formula (V)

$$M-Q-R^3 \quad \text{(V)}$$

in which

Q and $R^3$ are each as defined above and

M represents hydrogen or a metal equivalent, if appropriate in the presence of a reaction auxiliary and if appropriate in the presence of a diluent.

The novel substituted aminouracils of the general formula (I) have strong herbicidal properties.

In the definitions, the saturated or unsaturated hydrocarbon chains, such as alkyl, alkenyl or alkinyl, are in each case split-chain or branched.

Halogen generally represents fluorine, chlorine, bromine or iodine, preferably fluorine, chlorine or bromine, in particular fluorine or chlorine.

The invention preferably provides compounds of the formula (I) in which

Q represents O, S, SO or $SO_2$, $R^1$ represents hydrogen, cyano, fluorine or chlorine, $R^2$ represents cyano or thiocarbamoyl, $R^3$ represents hydrogen, represents alkyl, alkenyl or alkinyl of in each up to 10 carbon atoms, each of which is optionally substituted by cyano, carboxy, fluorine, chlorine, bromine, or by $C_1$–$C_4$-alkoxy, $C_1$–$C_4$-alkylcarbonyl, $C_1$–$C_4$-alkoxycarbonyl or N-($C_1$–$C_4$-alkyl)-N-phenyl-aminocarbonyl (each of which is optionally substituted by fluorine and/or chlorine)

$R^3$ furthermore represents cycloalkyl or cycloalkylalkyl of 3 to 8 carbon atoms in the cycloalkyl moiety and optionally up to 4 carbon atoms in the alkyl moiety, each of which is optionally substituted by cyano, carboxy, fluorine, chlorine, bromine, $C_1$–$C_4$-alkyl, $C_1$–$C_4$-alkoxy, $C_1$–$C_4$-alkyl-carbonyl or $C_1$–$C_4$-alkoxy-carbonyl, $R^3$ furthermore represents aryl or arylalkyl of 6 or 10 carbon atoms in the aryl moiety and optionally up to 4 carbon atoms in the alkyl moiety, each of which is optionally substituted by cyano, carboxy, nitro, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl or $C_1$–$C_4$-alkoxy-carbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), or $R^3$ furthermore represents furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, each of which is optionally substituted by cyano, carboxy, carbamoyl, thiocarbamoyl, fluorine, chlorine, bromine, by $C_1$–$C_4$-alkyl, $C_1$–$C_4$-alkoxy, $C_1$–$C_4$-aklythio, $C_1$–$C_4$-alkylsulphinyl, $C_1$–$C_4$-alkylsulphonyl, $C_1$–$C_4$-alkylcarbonyl or $C_1$–$C_4$-alkoxy-carbonyl (each of which is optionally substituted by fluorine and/or chlorine), by phenyl, phenoxy or phenylthio (each of which is optionally substituted by fluorine, chlorine, bromine, cyano, methyl, methoxy, trifluoromethyl and/or trifluoromethoxy), $R^4$ represents hydrogen, fluorine, chlorine, bromine or represents respectively optionally fluorine- and/or chlorine-substituted alkyl or alkoxy having in each case 1 to 4 carbon atoms, $R^5$ represents optionally fluorine- and/or chlorine-substituted alkyl having 1 to 4 carbon atoms, $R^6$ represents hydrogen or represents respectively optionally fluorine-, chlorine- or $C_1$–$C_4$-alkoxy-substituted alkyl, alkenyl or alkinyl having in each case up to 6 carbon atoms, and $R^7$ represents hydrogen or represents respectively optionally fluorine-, chlorine- or $C_1$–$C_4$-alkoxy-substituted alkyl, alkenyl or alkinyl having in each case up to 6 carbon atoms.

The invention in particular provides compounds of the formula (I) in which

Q represents O, S, SO or $SO_2$, $R^1$ represents hydrogen, fluorine or chlorine, $R^2$ represents cyano or thiocarbamoyl, $R^3$ represents hydrogen, represents respectively optionally cyano-, carboxy-, fluorine-, chlorine-, methoxy-, ethoxy-, n- or i-propoxy-, acetyl-, propionyl-, methoxycarbonyl-, ethoxycarbonyl-, n- or i-propoxycarbonyl-substituted methyl, ethyl, n- or i-propyl, n-, i-, s- or t-butyl-, n-, i-, s- or t-pentyl, propenyl, butenyl, pentenyl, propinyl, butinyl or pentinyl, represents respectively optionally cyano-, carboxy-, fluorine-, chlorine-, bromine-methyl-, ethyl-, n- or i-propyl-, methoxy-, ethoxy-, n- or i-propoxy-, acetyl- or propionyl-, methoxycarbonyl-, ethoxycarbonyl-, n- or i-propoxycarbonyl-substituted cyclopropyl, cyclobutyl, cyclopentyl, cyclohexyl, cyclopropylmethyl, cyclobutylmethyl, cyclopentylmethyl or cyclohexylmethyl, represents respectively optionally cyano-, carboxy-, nitro-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-substituted phenyl, benzyl or phenylethyl, or represents respectively optionally cyano-, carboxy-, carbamoyl-, thiocarbamoyl-, fluorine-, chlorine-, bromine-, methyl-, ethyl-, n- or i-propyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, phenyl-, phenoxy- or phenylthio-substituted furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, $R^4$ represents hydrogen, fluorine, chlorine, bromine or methyl, $R^5$ represents methyl, ethyl, difluoromethyl, dichloromethyl, trifluoromethyl, trichloromethyl, chlorodifluoromethyl, fluorodichloromethyl, chloroethyl, fluoroethyl, dichloroethyl, difluoroethyl, chlorofluoroethyl, chlorodifluoroethyl, fluorodichloroethyl, trifluoroethyl, tetrafluoroethyl, chlorotrifluoroethyl or pentafluoroethyl, $R^6$ represents hydrogen or represents respectively optionally fluorine-, chlorine-, methoxy- or ethoxy-substituted methyl, ethyl, n- or i-propyl, n-, i-, s- or t-butyl-propenyl, butenyl, propinyl or butinyl, and $R^7$ represents hydrogen or represents respectively optionally fluorine-, chlorine-, methoxy- or ethoxy-substituted methyl, ethyl, n- or i-propyl, n-, i-, s- or t-butyl, propenyl, butenyl, propinyl or butinyl.

The general or preferred radical definitions listed above are valid both for the end products of the formula (I) and also, in a corresponding manner, for the starting materials or intermediates which are required in each case for the preparation. These radical definitions can be combined with each other at will, i.e. including combinations between the given preferred ranges.

Examples of compounds of the formula (I) according to the invention are listed in the groups below.

Group 1

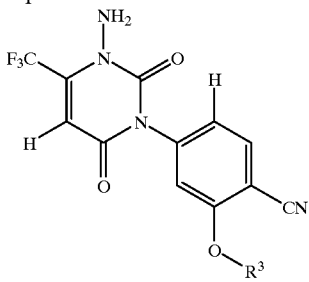

R³ has for example the meanings given in the list below:
hydrogen, methyl, ethyl, n- or i-propyl, n-, i-, s- or t-butyl, n-, i-, s- or t-pentyl, difluoromethyl, trifluoromethyl, chlorodifluoromethyl, fluorodichloromethyl, fluoroethyl, chloroethyl, chlorofluoroethyl, difluoroethyl, dichloroethyl, trifluoroethyl, trichloroethyl, chlorodifluoroethyl, tetrafluoroethyl, chlorotrifluoroethyl, pentafluoroethyl, fluoropropyl, chloropropyl, difluoropropyl, dichloropropyl, trifluoropropyl, trichloropropyl, cyanomethyl, cyanoethyl, cyanopropyl, cyanobutyl, carboxymethyl, carboxyethyl, carboxypropyl, carboxybutyl, methoxymethyl, ethoxymethyl, propoxymethyl, methoxyethyl, ethoxyethyl, propoxyethyl, methoxypropyl, ethoxypropyl, propoxypropyl, methoxycarbonylmethyl, ethoxycarbonylmethyl, propoxycarbonylmethyl, methoxycarbonylethyl, ethoxycarbonylethyl, propoxycarbonylethyl, methoxycarbonylpropyl, ethoxycarbonylpropyl, propoxycarbonylpropyl, 1-propen-3-yl (allyl), 3-methyl-1-propen-3-yl, 2-buten-4-yl (crotonyl), 1-propin-3-yl (propargyl), 3-methyl-1-propin-3-yl, 2-butin-4-yl, cyclopropyl, cyanocyclopropyl, carboxycyclopropyl, difluorocyclopropyl, dichlorocyclopropyl, methylcyclopropyl, methoxycarbonylcyclopropyl, ethoxycarbonylcyclopropyl, cyclobutyl, cyanocyclobutyl, carboxycyclobutyl, difluorocyclopropyl, trifluorocyclobutyl, tetrafluorocyclobutyl, chlorotrifluorocyclobutyl, methylcyclobutyl, cyclopentyl, cyanocyclopentyl, carboxycyclopentyl, fluorocyclopentyl, chlorocyclopentyl, difluorocyclopentyl, dichlorocyclopentyl, methylcyclopentyl, methoxycarbonylcyclopentyl, ethoxycarbonylcyclopentyl, cyclohexyl, cyanocyclohexyl, carboxycyclohexyl, fluorocyclohexyl, chlorocyclohexyl, difluorocyclohexyl, dichlorocyclohexyl, methylcyclohexyl, trifluoromethylcyclohexyl, methoxycarbonylcyclohexyl, ethoxycarbonylcyclohexyl, cyclopropylmethyl, difluorocyclopropylmethyl, dichlorocyclopropylmethyl, cyclobutylmethyl, cyclopentylmethyl, cyclohexylmethyl, cyanocyclohexylmethyl, carboxycyclohexylmethyl, fluorocyclohexylmethyl, chlorocyclohexylmethyl, methylcyclohexylmethyl, trifluoromethylcyclohexylmethyl, phenyl, cyanophenyl, carboxyphenyl, nitrophenyl, fluorophenyl, chlorophenyl, bromophenyl, methylphenyl, trifluoromethylphenyl, methoxyphenyl, difluoromethoxyphenyl, trifluoromethoxyphenyl, methoxycarbonylphenyl, ethoxycarbonylphenyl, benzyl, cyanobenzyl, carboxybenzyl, fluorobenzyl, chlorobenzyl, methylbenzyl, trifluoromethylbenzyl, methoxybenzyl, difluoromethoxybenzyl, trifluoromethoxybenzyl, methoxycarbonylbenzyl, ethoxycarbonylbenzyl, phenylethyl, furyl, tetrahydrofuryl, thienyl, tetrahydrothienyl, oxetanyl, oxazolyl, isoxazolyl.

Group 2

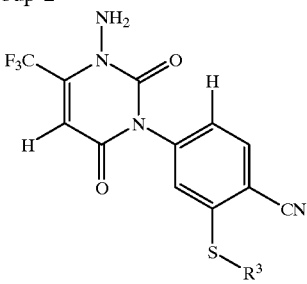

R³ has for example the meanings given above in group 1.

Group 3

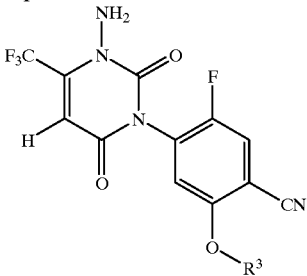

R³ has for example the meanings given above in group 1.

Group 4

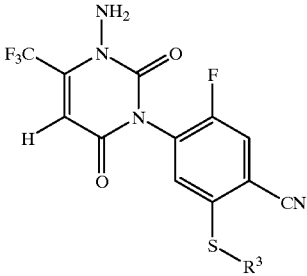

R³ has for example the meanings given above in group 1.

Group 5

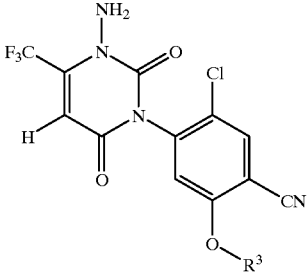

R³ has for example the meanings given above in group 1.

Group 6

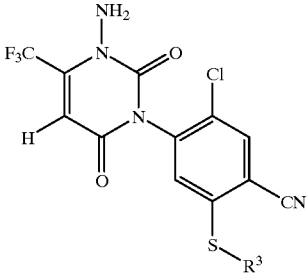

R³ has for example the meanings given above in group 1.

Group 7

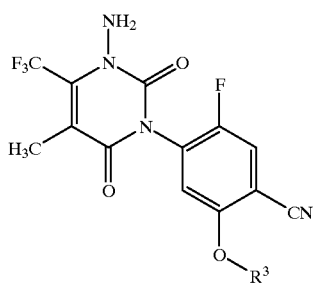

R³ has for example the meanings given above in group 1.

Group 8

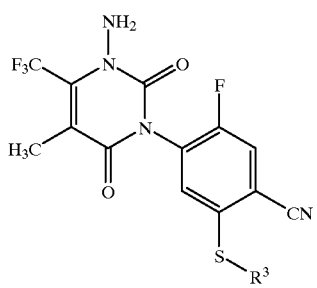

R³ has for example the meanings given above in group 1.

Group 9

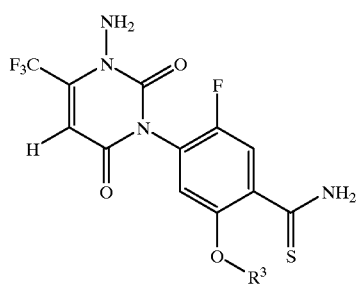

R³ has for example the meanings given above in group 1.

Group 10

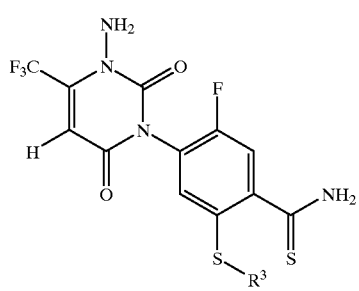

R³ has for example the meanings given above in group 1.

Group 11

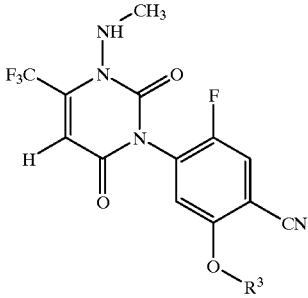

R³ has for example the meanings given above in group 1.

Group 12

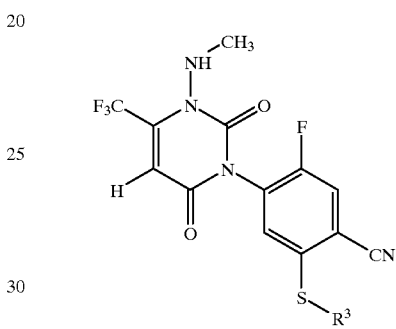

R³ has for example the meanings given above in group 1.

Group 13

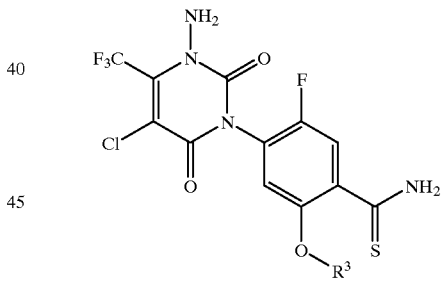

R³ has for example the meanings given above in group 1.

Group 14

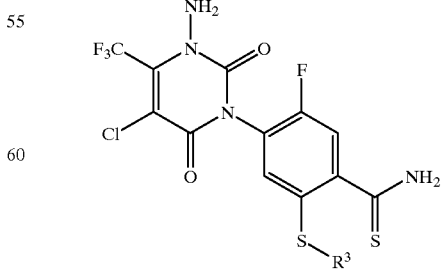

R³ has for example the meanings given above in group 1.

Group 15

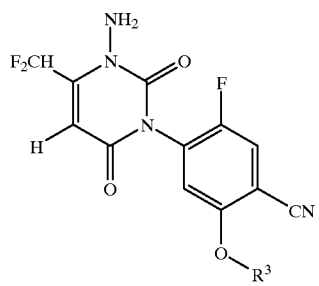

R³ has for example the meanings given above in group 1.
Group, 16

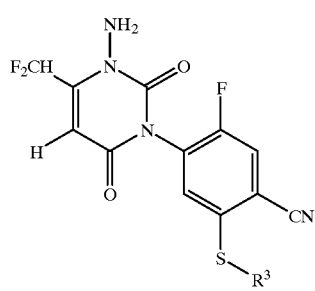

R³ has for example the meanings given above in group 1.
Group 17

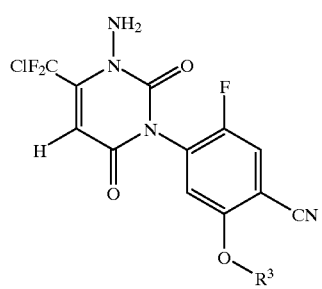

R³ has for example the meanings given above in group 1.
Group 18

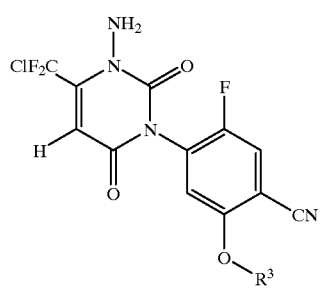

R³ has for example the meanings given above in group 1.

Group 19

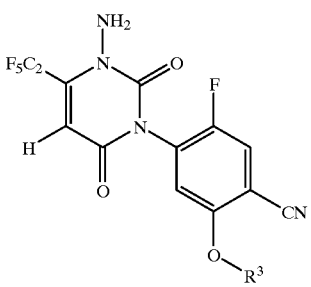

R³ has for example the meanings given above in group 1.
Group 20

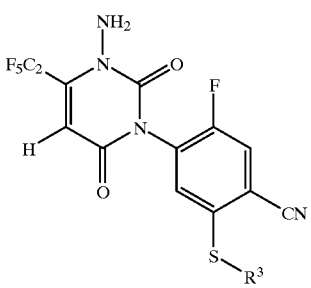

R³ has for example the meanings given above in group 1.
Using, for example, 1(2-chloro-4-cyano-5-cyanomethoxy-phenyl)-3,6-dihydro-2,6-dioxo-4-difluoromethyl-1(2H)-pyrimidine as starting material and 1-aminooxy-2,4-dinitro-benzene as electrophilic aminating agent, the course of the reaction in the process (a) according to the invention can be illustrated by the following scheme:

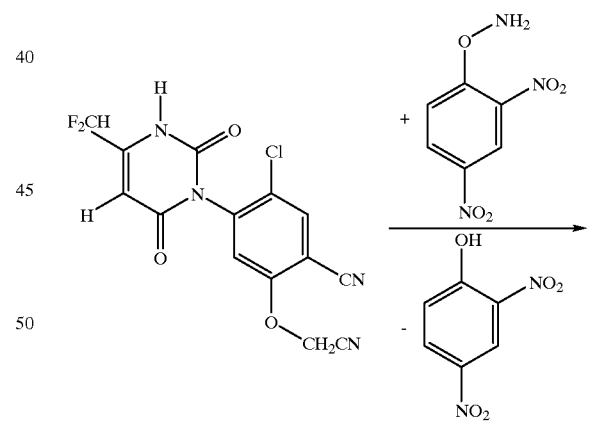

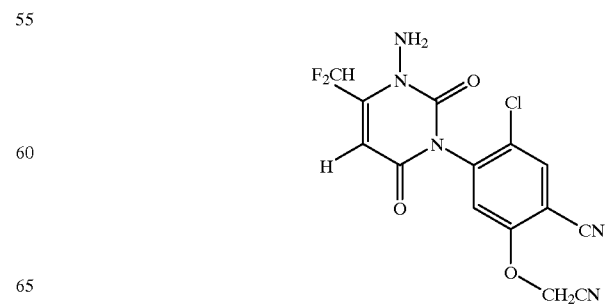

Using, for example, 1-(4-cyano-5-difluoromethoxy-phenyl)-3,6-dihydro-2,6-dioxo-3-amino-4-chlorodifluoromethyl-1(2H)-pyrimidine as starting material, the course of the reaction in the process (b) according to the invention can be illustrated by the following scheme:

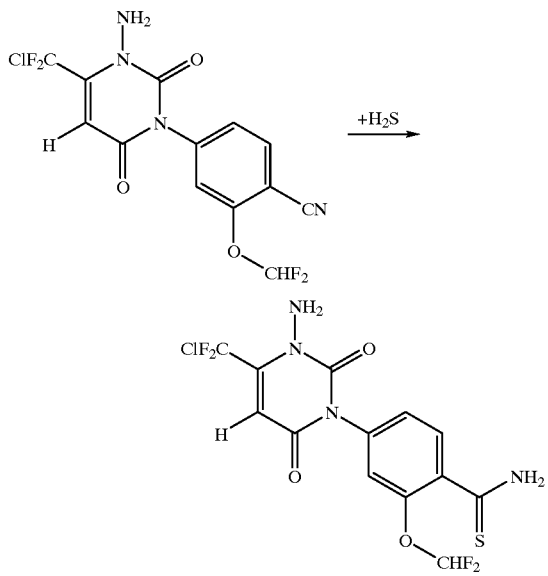

Using, for example, 1-(4-cyano-5-ethylthio-2-fluoro-phenyl)-3,6-dihydro-2,6-dioxo-3-amino-5-methyl-4-trifluoromethyl-1(2H)-pyrimidine and methyl bromide as starting materials, the course of the reaction in the process (c) according to the invention can be illustrated by the following scheme:

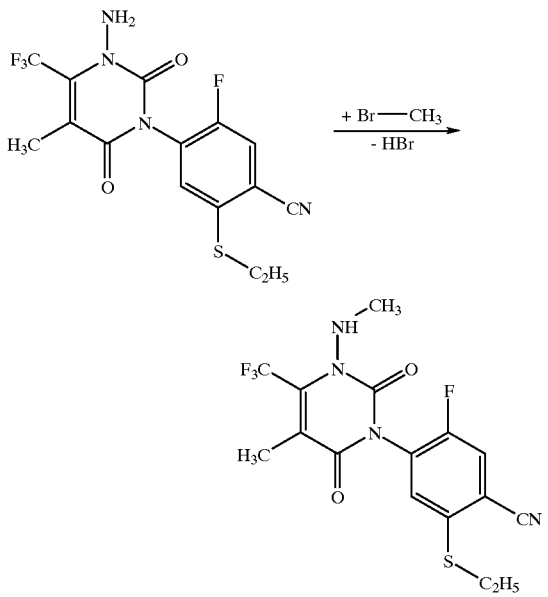

Using, for example, 1-(4-cyano-2,5-difluoro-phenyl)-3,6-dihydro-2,6-dioxo-5-chloro4-trifluoromethyl-1(2H)-pyrimidine and sodium methoxide as starting materials, the course of the reaction in the process (d) can be illustrated by the following scheme:

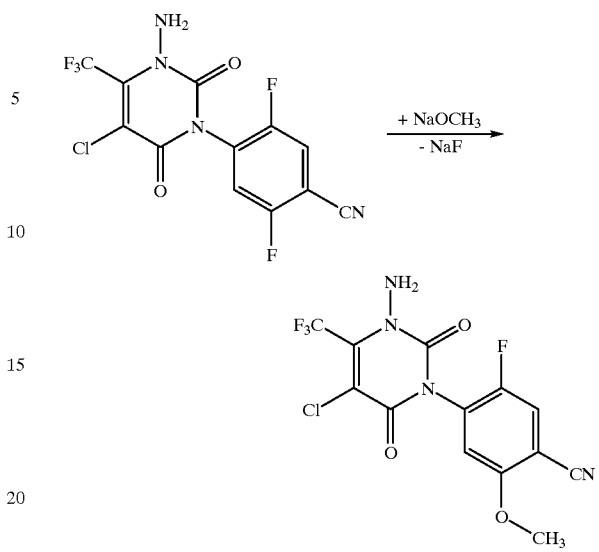

The formula (II) provides a general definition of the substituted uracils to be used as starting materials in the process (a) according to the invention for preparing the compounds of the formula (I). In the formula (II), Q, $R^1$, $R^2$, $R^3$, $R^4$ and $R^5$ each preferably or in particular have those meanings which have already been indicated above, in connection with the description of compounds of the formula (I) to be prepared according to the invention, as being preferred or particularly preferred for Q, $R^1$, $R^2$, $R^3$, $R^4$ and $R^5$.

The starting materials of the formula (II) are known and/or can be prepared by known methods (cf. EP 408382, Preparation Examples).

The process (a) according to the invention is carried out using an electrophilic aminating agent. Suitable aminating agents are the customary electrophilic aminating agents. Examples include 1-aminooxy-2,4-dinitro-benzene (2,4-dinitro-phenyl-hydroxylamine) and hydroxylamine-O-sulfonic acid.

The formula (Ia) provides a general definition of the aminouracils to be used as starting materials in the process (b) according to the invention for preparing compounds of the formula (I). In the formula (Ia), Q, $R^1$, $R^3$, $R^4$, $R^5$, $R^6$ and $R^7$ each preferably or in particular have those meanings which have already been indicated above, in connection with the description of the compounds of the formula (I) to be prepared according to the invention, as being preferred or particularly preferred for Q, $R^1$, $R^3$, $R^4$, $R^5$, $R^6$ and $R^7$.

The starting materials of the formula (Ia) are novel compounds according to the invention; they can be prepared by the processes (a) or (c) according to the invention.

The formula (Ib) provides a general definition of the aminouracils to be used as starting materials in the process (c) according to the invention for preparing the compounds of the formula (I). In the formula (Ib), Q, $R^1$, $R^2$, $R^3$, $R^4$ and $R^5$ each preferably or in particular have those meanings which have already been indicated above, in connection with the description of the compounds of the formula (I) to be prepared according to the invention, as being preferred or particularly preferred for Q, $R^1$, $R^2$, $R^3$, $R^4$ and $R^5$.

The starting materials of the formula (Ib) are novel compounds according to the invention; they can be prepared by the processes (a) or (b) according to the invention.

The formulae (IIIa) and (IIIb) provide general definitions of the alkylating agents further to be used as starting materials in the process (c) according to the invention for preparing the compounds of the formula (I). In the formulae (IIIa) and (IIIb), $R^7$ and $R^8$ each preferably or in particular have those meanings which have already been indicated above, in connection with the description of the compounds of the formula (I) to be prepared according to the invention, as being preferred or particularly preferred for $R^7$ and $R^8$; X preferably represents fluorine, chlorine, bromine or iodine, in particular chlorine, bromine or iodine.

The formula (IV) provides a general definition of the aminouracils to be used as starting materials in the process (d) according to the invention for preparing the compounds of the formula (I). In the formula (IV), $R^1$, $R^2$, $R^4$, $R^5$, $R^6$ and $R^7$ each preferably or in particular have those meanings which have already been indicated above, in connection with the description of the compounds of the formula (I) to be prepared according to the invention, as being preferred or particularly preferred for $R^1$, $R^2$, $R^4$, $R^5$, $R^6$ and $R^7$; X preferably represents fluorine, chlorine or bromine, in particular fluorine or chlorine.

The starting materials of the formula (IV) are known and/or can be prepared by known methods (cf. EP 648749).

The formula (V) provides a general definition of the nucleophilic compounds further to be used as starting materials in the process (d) according to the invention for preparing the compounds of the formula (I). In the formula (V), Q and $R^3$ each preferably or in particular have those meanings which have already been indicated above, in connection with the description of the compounds of the formula (I) to be prepared according to the invention, as being preferred or particularly preferred for Q and $R^3$; M preferably represents lithium, sodium, potassium.

The starting materials of the formula (V) are known chemicals for synthesis.

The processes (a), (b), (c) and (d) according to the invention for preparing the compounds of the formula (I) are preferably carried out in the presence of a suitable reaction auxiliary. Suitable reaction auxiliaries are generally the customary inorganic or organic bases or acid acceptors. These include preferably alkali metal or alkaline earth metal acetates, amides, carbonates, bicarbonates, hydrides, hydroxides or alkoxides such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylamino-pyridine, N-methylpiperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

The processes (a), (b), (c) and (d) according to the invention for preparing the compounds of the formula (I) are preferably carried out in the presence of a diluent. Suitable diluents are generally the customary organic solvents. These preferably include aliphatic, alicyclic and aromatic, optionally halogenated hydrocarbons such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or tetrachloromethane, dialkyl ethers such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones, such as, for example, acetone, butanone (methyl ethyl ketone), methyl i-propyl ketone or methyl i-butyl ketone, nitriles such as, for example, acetonitrile, propionitrile, butyronitrile or benzonitrile; amides such as, for example, N,N-dimethyl-formamide (DMF), N,N-dimethyl-acetamide, N-methyl-formanilide, N-methyl-pyrrolidone or hexamethyl-phosphoric triamide; esters such as, for example, methyl acetate, ethyl acetate, n- or i-propyl acetate, n-, i- or s-butyl acetate; sulphoxides such as, for example, dimethyl sulphoxide; alkanols such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; mixtures thereof with water or pure water.

When carrying out the processes (a), (b), (c) and (d) according to the invention, the reaction temperatures can be varied over a relatively wide range. In general, temperatures of between −20° C. and +150° C., preferably between 0° C. and 120° C., are employed.

The processes (a), (b), (c) and (d) according to the invention are generally carried out under atmospheric pressure. However, it is also possible to carry out the processes according to the invention under elevated or reduced pressure—in general between 0.1 bar and 10 bar.

In the practice of the processes (a), (b), (c) and (d) according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out according to customary methods (cf. the Preparation Examples).

The active compounds according to the invention can be used as defoliants, desiccants, haulm-killers and, especially, as weed-killers. Weeds, in the broadest sense, are all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds of the formula (I) are suitable, depending on the concentration, for the total control of weeds, for example on industrial terrain and rail tracks, and on paths and squares with or without tree plantings. Equally, the compounds of the formula (I) according to the invention can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyledonous weeds in monocotyledonous crops and dicotyledenous crops, both by the pre- and the post-emergence method.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, it is also possible to use for example organic solvents as auxiliary solvents. Essentially, suitable liquid solvents are aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates, suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be used as such or, in their formulations, as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichiobenil and ioxynil; oxyacetamides such as, for example, mefenacet; sulfonylureas such as, for example, amido-sulfuron, bensulfuron-methyl, chlorimuron-ethyl, chlorsulfuron, cinosulfuron, metsulfuron-methyl, nicosulfuron, primisulfuron, pyrazosulfuron-ethyl, thifen-sulfuron-methyl, triasulfuron and tribenuron-methyl; thiocarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, amino-triazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

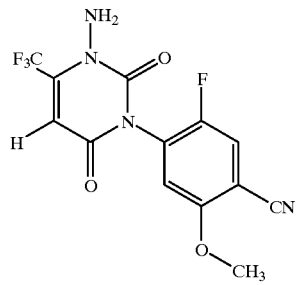

(Process (a))

A mixture of 2.0 g (6 mmol) of 1-(4-cyano-2-fluoro-5-methoxy-phenyl)-3,6-dihydro-2,6-dioxo-4-trifluoromethyl-1(2H)-pyrimidine, 0.5 g (6 mmol) of sodium bicarbonate and 10 ml of dimethylformamide is stirred at 20° C. for 1 hour. 0.6 g (3 mmol) of 1-aminooxy-2,4-dinitro-benzene is then added and the reaction mixture is stirred at 20° C. for 24 hours. After the addition of a further 0.3 g (1.5 mmol) of 1-aminooxy-2,4-dinitro-benzene, the mixture is stirred for 3 days; a further 0.3 g (1.5 mmol) of 1-aminooxy-2,4-dinitro-benzene are then added and stirring is continued for a further 3 days. 50 ml of ethyl acetate and 50 ml of saturated aqueous sodium chloride solution are then added to the mixture. The mixture is shaken, the organic phase is separated off and the aqueous phase is re-extracted three times with ethyl acetate. The combined organic solutions are washed twice with water, dried with sodium sulphate, filtered through 5 cm of silica gel and washed with 300 ml of ethyl acetate. The filtrate is concentrated using water pump vacuum, the residue is titrated with ethyl acetate and the crystalline product is isolated by filtration.

1.1 g (53% of theory) of 1-(4-cyano-2-fluoro-5-methoxy-phenyl)-3,6-dihydro-2,6-dioxo-3-amino-4-trifluoromethyl-1(2H)-pyrimidine of melting point 241° C. are obtained.

Similar to Example 1 and according to the general description of the preparation processes according to the invention, it is also possible to prepare, for example, the compounds of the formula (I) listed in Table 1 below

TABLE 1

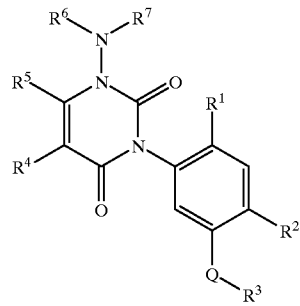

Examples of compounds of the formula (I)

| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 2 | O | H | CN | $CH_3$ | H | $CF_3$ | H | H | |
| 3 | O | F | $CSNH_2$ | $CH_3$ | H | $CF_3$ | H | H | |
| 4 | O | F | CN | $C_2H_5$ | H | $CF_3$ | H | H | 68 |
| 5 | O | F | $CSNH_2$ | $C_2H_5$ | H | $CF_3$ | H | H | |
| 6 | O | F | CN | $-CH_2-CH=CH_2$ | H | $CF_3$ | H | H | (amorphous) |
| 7 | O | F | CN | $-CH_2-C{\equiv}CH$ | H | $CF_3$ | H | H | (amorphous) |

TABLE 1-continued

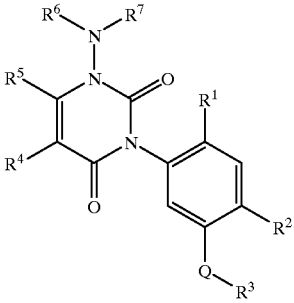

Examples of compounds of the formula (I)

| Ex. No. | Q | R¹ | R² | R³ | R⁴ | R⁵ | R⁶ | R⁷ | Melting point (° C.) |
|---|---|---|---|---|---|---|---|---|---|
| 8 | O | F | CN | 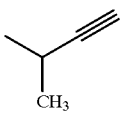 | H | CF₃ | H | H | |
| 9 | S | F | CN | CH₃ | H | CF₃ | H | H | |
| 10 | S | F | CN | CH₂C₆H₅ | H | CF₃ | H | H | |
| 11 | O | F | CN | CH₂C₆H₅ | H | CF₃ | H | H | 62 |
| 12 | O | F | CSNH₂ | CH₂C₆H₅ | H | CF₃ | H | H | |
| 13 | O | F | CN | H | H | CF₃ | H | H | |
| 14 | O | F | CN | 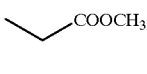 | H | CF₃ | H | H | |
| 15 | O | F | CN | 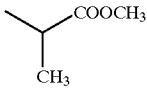 | H | CF₃ | H | H | |
| 16 | O | F | CN | 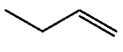 | CH₃ | CF₃ | H | H | |
| 17 | O | F | CN | 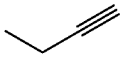 | CH₃ | CF₃ | H | H | |
| 18 | O | F | CN | 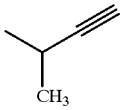 | CH₃ | CF₃ | H | H | |
| 19 | O | F | CN | CH₃ | H | CF₃ | CH₃ | CH₃ | |
| 20 | O | F | CN | CH₃ | H | CF₃ | H | CH₃ | |
| 21 | O | F | CN | CH₃ | H | CHF₂ | H | H | |
| 22 | O | F | CN | CH₃ | H | CFCl₂ | H | H | |
| 23 | O | H | CN | 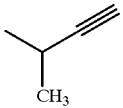 | H | CF₃ | H | H | |
| 24 | O | H | CN | 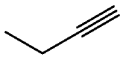 | H | CF₃ | H | H | |
| 25 | S | H | CN | 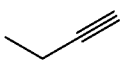 | Cl | CF₃ | H | CH₃ | |
| 26 | O | F | CN | C₃H₇-i | H | CF₃ | H | H | |
| 27 | O | F | CSNH₂ | C₃H₇-i | H | CF₃ | H | H | |

TABLE 1-continued

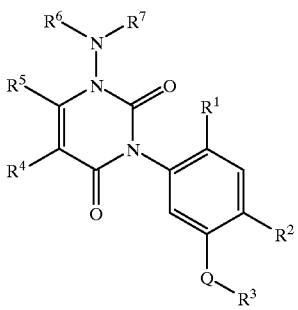

Examples of compounds of the formula (I)

| Ex. No. | Q | $R^1$ | $R^2$ | $R^3$ | $R^4$ | $R^5$ | $R^6$ | $R^7$ | Melting point (° C.) |
|---|---|---|---|---|---|---|---|---|---|
| 28 | S | F | CN | $C_3H_7$-n | H | $CF_3$ | H | H | |
| 29 | S | F | $CSNH_2$ | $C_3H_7$-n | H | $CF_3$ | H | H | |
| 30 | S | F | CN | H | H | $CF_3$ | H | H | |
| 31 | O | F | $CSNH_2$ | H | H | $CF_3$ | H | H | |
| 32 | S | F | $CSNH_2$ | H | H | $CF_3$ | H | H | |
| 33 | O | F | CN | —CH₂—C(O)—N(CH(CH₃)₂)(phenyl) | H | $CF_3$ | H | H | 186 |
| 34 | O | F | CN | cyclopentyl-CH₂— | H | $CF_3$ | H | H | |
| 35 | O | F | CN | cyclohexyl-CH₂— | H | $CF_3$ | H | H | 227 |
| 36 | O | F | CN | oxetanyl-CH₂— | H | $CF_3$ | H | H | 196 |

Starting materials of formula (II):

Example (II-1)

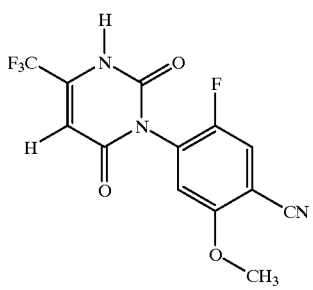

A mixture of 3.8 g (12 mmol) of 1-(4-cyano-2,5-difluorophenyl)-3,6-dihydro-2,6-dioxo-4-trifluoromethyl-1(2H)-pyrimidine, 1.5 g (21 mmol) of sodium methoxide and 50 ml of N-methyl-pyrrolidone is stirred at 130° C. for 36 hours. The mixture is cooled and diluted with ethyl acetate to about three times its volume and washed with water, and the product is isolated by silica gel column chromatography (cyclohexane/ethyl acetate 1/1 (v/v)).

1.6 g (41% of theory) of 1-(4-cyano-2-fluoro-5-methoxyphenyl)-3,6-dihydro-2,6-dioxo-4-trifluoromethyl-1(2H)-pyrimidine of melting point 114° C. are obtained.

Use Examples

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with a stated amount of solvent, the stated amount of the emulsifier is added and the concentrate is diluted with water to the desired concentration.

Seeds of the test plants are sown in normal soil. After about 24 hours, the soil is watered with the preparation of the active compound. It is advantageous to keep the amount of water per unit area constant. The concentration of the active compound in the preparation is immaterial, only the amount of active compound applied per unit area matters.

After three weeks, the degree of damage to the plants is rated in % damage by comparison with the development of the untreated control.

The figures denote:

0%=no effect (like untreated control)

100%=total destruction

In this test, virtually complete destruction of a large number of weeds such as, for example, Alopecurus (100%), Avena (100%), Cyperus (100%), Setaria (100%), Abutilon (100%), Amaranthus (100%), Galium (100%), Sinapis (100%), Xanthium (100%) was effected, for example, by the compound of Preparation Example 1 at an application rate of 125 g/ha.

and the concentrate is diluted with water to the desired concentration.

Test plants which have a height of 5–15 cm are sprayed with the preparation of the active compound in such a way as to apply the particular amounts of active compound desired per unit area.

After three weeks, the degree of damage to the plants is rated in % damage by comparison with the development of the untreated control.

TABLE A

Pre-emergence-test/greenhouse

| active ingredient | a.i. (g/ha) | Alopecurus | Avena | Cyperus | Setaria | Abutilon | Amaranthus | Galium | Sinapis | Xanthium |
|---|---|---|---|---|---|---|---|---|---|---|
| (1) | 125 | 100 | 100 | 100 | 100 | 100 | 100 | 100 | 100 | 100 |

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added The figures denote:

0%=no effect (like untreated control)

100%=total destruction

In this test, virtually complete destruction of a large number of weeds such as, for example, Alopecurus (100%), Avena (100%), Cyperus (100%), Setaria (100%), Abutilon (100%), Amaranthus (100%), Galium (100%), Sinapis (100%) and Xanthium (100%) was effected, for example, by the compound of Preparation Example 1 at an application rate of 125 g/ha.

TABLE B

Post-emergence-test/greenhouse

| active ingredient | a.i. (g/ha) | Alopecurus | Avena | Cyperus | Setaria | Abutilon | Amaranthus | Galium | Sinapis | Xanthium |
|---|---|---|---|---|---|---|---|---|---|---|
| (1) | 125 | 100 | 100 | 100 | 100 | 100 | 100 | 100 | 100 | 100 |

What is claimed is:

1. A substituted aminouracil of formula (I)

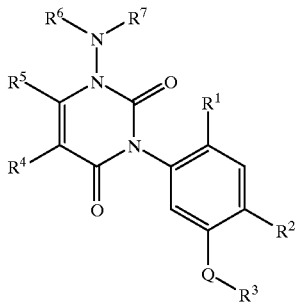

(I)

wherein

Q represents O, S, SO or $SO_2$;

$R^1$ represents hydrogen, cyano, fluorine or chlorine;

$R^2$ represents cyano;

$R^3$ represents aryl with 6 or 10 carbon atoms which is optionally substituted by cyano, carboxy, nitro, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl each of which is optionally substituted by fluorine or chlorine, by phenyl, phenoxy or phenylthio each of which is optionally substituted by fluorine, chlorine, bromine, cyano, methyl, methoxy, trifluoromethyl or trifluoromethoxy; or furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, each of which is optionally substituted by cyano, carboxy, carbamoyl, thiocarbamoyl, fluorine, chlorine, bromine, by $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl each of which is optionally substituted by fluorine or chlorine), by phenyl, phenoxy or phenylthio each of which is optionally substituted by fluorine, chlorine, bromine, cyano, methyl, methoxy, trifluoromethyl or trifluoromethoxy;

$R^4$ represents hydrogen, fluorine, chlorine, bromine or represents respectively optionally fluorine- or chlorine-substituted alkyl or alkoxy having in each case 1 to 4 carbon atoms;

$R^5$ represents optionally fluorine- or chlorine-substituted alkyl having 1 to 4 carbon atoms;

$R^6$ represents hydrogen or represents respectively optionally fluorine-, chlorine- or $C_1$–$C_4$-alkoxy-substituted alkyl, alkenyl or alkinyl having in each case up to 6 carbon atoms; and $R^7$ represents hydrogen or represents respectively optionally fluorine-, chlorine- or $C_1$–$C_4$-alkoxy-substituted alkyl, alkenyl or alkinyl having in each case up to 6 carbon atoms.

2. The substituted aminouracil of claim 1 wherein

Q represents O, S, SO or $SO_2$, $R^1$ represents hydrogen, fluorine or chlorine;

$R^2$ represents cyano;

$R^3$ represents phenyl optionally substituted with a moiety selected from the group consisting cyano-, carboxy-, nitro-, carbamoyl-, thiocarbamoyl-, fluorine-, chlorine-, bromine-, methyl-, ethyl-, n- or i-propyl, n-, i-, s- or t-butyl-, trifluoromethyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-; or represents furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, optionally substituted with a moiety selected from the group consisting of cyano-, carboxy-, carbamoyl-, thiocarbamoyl-, fluorine-, chlorine-, bromine-, methyl-, ethyl-, n- or i-propyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, phenyl-, phenoxy- or phenylthio-;

$R^4$ represents hydrogen, fluorine, chlorine, bromine or methyl, $R^5$ represents methyl, ethyl, difluoromethyl, dichloromethyl, trifluoromethyl, trichloromethyl, chlorodifluoromethyl, fluorodichloromethyl, chloroethyl, fluoroethyl, dichloroethyl, difluoroethyl, chlorofluoroethyl, chlorodifluoroethyl, fluorodichloroethyl, trifluoroethyl, tetrafluoroethyl, chlorotrifluoroethyl or pentafluoroethyl, $R^6$ represents hydrogen or represents respectively optionally fluorine-, chlorine-, methoxy- or ethoxy-substituted methyl, ethyl, n- or i-propyl, n-, i-, s- or t-butyl-, propenyl, butenyl, propinyl or butinyl, and $R^7$ represents hydrogen or represents respectively optionally fluorine-, chlorine-, methoxy- or ethoxy-substituted methyl, ethyl, n- or i-propyl, n-, i-, s- or t-butyl, propenyl, butenyl, propinyl or butinyl.

3. A process for preparing the substituted aminouracils of the formula (I)

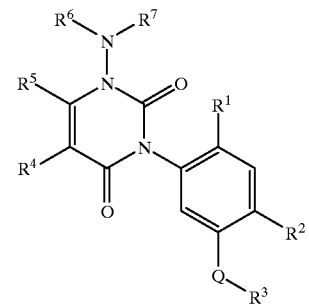

(I)

in which

Q, $R^1$, $R^2$, $R^4$, $R^5$, $R^6$ and $R^7$ are each as defined in claim 1, wherein a) substituted uracils of the formula (II)

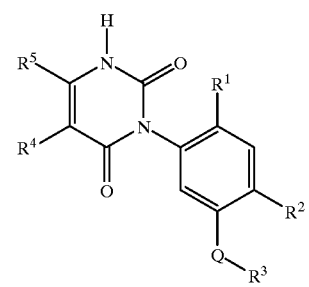

(II)

in which

Q, $R^1$, $R^2$, $R^3$, $R^4$ and $R^5$ are each as defined claim 1, are reacted with an electrophilic aminating agent, optionally in the presence of a reaction auxiliary, and optionally in the presence of a diluent; or (b) aminouracils of the formula (Ia)

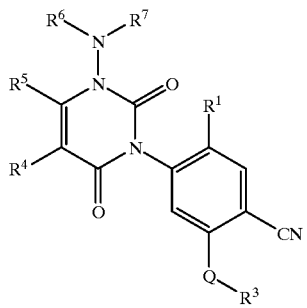

(Ia)

in which
Q, $R^1$, $R^3$, $R^4$, $R^5$, $R^6$ and $R^7$ defined claim 1,
are reacted with hydrogen sulphide, optionally in the presence of a reaction auxiliary and optionally in the presence of a diluent; or (c) aminouracils of the formula (1b)

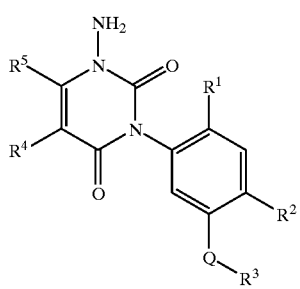

(Ib)

in which
Q, $R^1$, $R^2$, $R^3$, $R^4$ and $R^5$ are each as defined claim 1,
are reacted with alkylating agent of the formula (IIIa) or of the formula (IIIb)

$$X—R^7 \qquad (IIIa)$$

$$X—R^8 \qquad (IIIb)$$

in which
$R^7$ and $R^8$ are each as defined claim 1 and
X represents halogen or the grouping —O—SO$_2$—O—$R^7$ or —O—SO$_2$—O—$R^8$,
optionally in the presence of a reaction auxiliary and optionally in the presence of a diluent; or (d) aminouracils of the formula (IV)

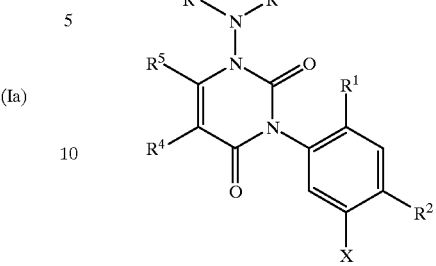

(IV)

in which
$R^1$, $R^2$, $R^4$, $R^5$, $R^6$ and $R^7$ are each as defined claim 1 and
X represents halogen,
are reacted with nucleophilic compounds of the formula (V)

$$M—Q—R^3 \qquad (V)$$

in which
Q and $R^3$ are each as defined above and
M represents hydrogen or a metal equivalent,
optionally in the presence of a reaction auxiliary and optionally in the presence of a diluent.

4. The aminouracils of formula (Ia)

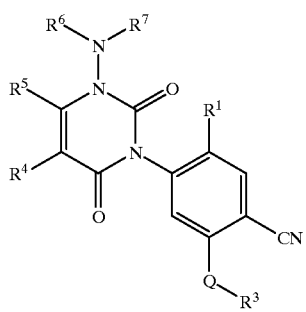

(Ia)

in which
Q represents O, S, SO or SO$_2$;
$R^1$ represents hydrogen, cyano or halogen;
$R^3$ represents optionally substituted aryl, or heterocyclyl;
$R^4$ represents hydrogen, halogen or represents respectively optionally substituted alkyl or alkoxy;
$R^5$ represents optionally substituted alkyl;
$R^6$ represents hydrogen or represents respectively optionally substituted alkyl, alkenyl or alkinyl; and
$R^7$ represents hydrogen or represents respectively optionally substituted alkyl, alkenyl or alkinyl.

5. An herbicidal composition comprising an herbicidally effective amount of a compound according to claim 1 and an extender.

6. A method of controlling unwanted vegetation which comprises applying to such vegetation or to a locus from which it is desired to exclude such vegetation an herbicidally effective amount of a compound according to claim 1.

* * * * *